United States Patent
Ide et al.

(10) Patent No.: US 10,995,133 B2
(45) Date of Patent: May 4, 2021

(54) METHOD FOR PRODUCING ANTIBODY

(71) Applicant: SYSMEX CORPORATION, Kobe (JP)

(72) Inventors: Nobuyuki Ide, Kobe (JP); Tomofumi Nakada, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 128 days.

(21) Appl. No.: 16/052,970

(22) Filed: Aug. 2, 2018

(65) Prior Publication Data
US 2019/0040119 A1 Feb. 7, 2019

(30) Foreign Application Priority Data
Aug. 4, 2017 (JP) ............... JP2017-151866

(51) Int. Cl.
| | | |
|---|---|---|
| *C07K 16/00* | (2006.01) | |
| *A61K 39/395* | (2006.01) | |
| *C07K 16/26* | (2006.01) | |
| *C07K 16/28* | (2006.01) | |
| *C07K 16/40* | (2006.01) | |
| *C12N 15/85* | (2006.01) | |

(52) U.S. Cl.
CPC .......... *C07K 16/005* (2013.01); *A61K 39/395* (2013.01); *C07K 16/00* (2013.01); *C07K 16/26* (2013.01); *C07K 16/2863* (2013.01); *C07K 16/40* (2013.01); *C07K 2317/22* (2013.01); *C07K 2317/24* (2013.01); *C07K 2317/565* (2013.01); *C07K 2317/567* (2013.01); *C07K 2317/569* (2013.01); *C07K 2317/624* (2013.01); *C07K 2317/90* (2013.01); *C07K 2317/92* (2013.01); *C07K 2317/94* (2013.01); *C07K 2318/00* (2013.01); *C12N 15/85* (2013.01); *C12N 2015/8518* (2013.01)

(58) Field of Classification Search
CPC C07K 2317/90; C07K 2317/94; C07K 16/00; A61K 39/395
USPC ........................................ 530/387.3
See application file for complete search history.

(56) References Cited

U.S. PATENT DOCUMENTS

| | | | |
|---|---|---|---|
| 2013/0303406 A1* | 11/2013 | Kim ........................ | A61P 35/00 506/18 |
| 2018/0179298 A1* | 6/2018 | Maeta ................... | C07K 16/40 |

FOREIGN PATENT DOCUMENTS

| | | |
|---|---|---|
| WO | 2007/109254 A3 | 9/2007 |
| WO | 2011/003811 A1 | 1/2011 |
| WO | 2012/100343 A1 | 8/2012 |
| WO | 2014/124316 A2 | 8/2014 |
| WO | 2014/124316 A3 | 8/2014 |

(Continued)

OTHER PUBLICATIONS

Worn and Pluckthun (J. Mol. Biol. (2001) 305, 989-1010).*

(Continued)

*Primary Examiner* — Lynn A Bristol
(74) *Attorney, Agent, or Firm* — Sughrue Mion, PLLC

(57) ABSTRACT

Disclosed is an antibody in which the 80th amino acid residue in a variable region based on the Kabat method and the 171th amino acid residue in a constant region based on the Kabat method are substituted with cysteine in an antibody in which the 80th amino acid residue in the variable region and the 171th amino acid residue in the constant region are not cysteine.

12 Claims, 5 Drawing Sheets

Specification includes a Sequence Listing.

(56) References Cited

FOREIGN PATENT DOCUMENTS

| WO | 2016/040856 A2 | 3/2016 |
|---|---|---|
| WO | 2016/040856 A3 | 3/2016 |

OTHER PUBLICATIONS

Kawade et al (Protein Engineering, Design & Selection, 2018, vol. 31 No. 7-8, pp. 243-247; Advance Access Publication Date: May 30, 2018).*
Tanabe et al (Biochemical and Biophysical Research Communications 496 (2018) 614-620).*
Popkov et al (J. Mol. Biol. (2003) 325, 325-335).*
TA INstruments (MCAPN-2011-06; pp. 1-3 (Sep. 13, 2020)).*
Yoshihisa Hagihara et al., "Engineering disulfide bonds within an antibody", Biochimica et Biophysica Acta, 2014, pp. 2016-2023, vol. 1844.
R. J. Poljak et al., "Three-Dimensional Structure of the Fab' Fragment of a Human Immunoglobulin at 2.8-A Resolution", Proc. Nat. Acad. Sci. USA, Dec. 1973, pp. 3305-3310, vol. 70, No. 12, Part I.
Romain Rouet et al., "Stability engineering of the human antibody repertoire", FEBS Letters, 2014, pp. 269-277, vol. 588.
Communication pursuant to Article 94(3) EPC dated Oct. 23, 2019 in a counterpart European patent application No. 18187164.1.
N. Martin Young et al., "Thermal stabilization of a single-chain Fv antibody fragment by introduction of a disulphide bond", FEBS Letters, vol. 377, No. 2, Dec. 18, 1995 (Dec. 18, 1995), pp. 135-139, 5 pages total.
Dirk Saerens et al., "Disulfide Bond Introduction for General Stabilization of Immunoglobulin Heavy-Chain Variable Domains", Journal of Molecular Biology, Academic Press, United Kingdom, vol. 377, No. 2, Jan. 15, 2008, pp. 478-488, XP022514628, 11 paes total.
Dan Zabetakis et al., "Evaluation of Disulfide Bond Position to Enhance the Thermal Stability of a Highly Stable Single Domain Antibody", PLOS ONE, vol. 9, No. 12, Dec. 19, 2014 (Dec. 19, 2014), p. e115405, XP055520397, 14 pages total.
Jean-Claude Jaton, "Amino Acid Sequence of the N-Terminal 139 Residues of Light Chain Derived from a Homogeneous Rabbit Antibody", Biochemical Journal, vol. 141, No. 1, Jul. 1, 1974 (Jul. 1, 1974), pp. 1-13, XP055520387, 13 pages total.
Hiromi Arai et al. "Crystal structure of a conformation-dependent rabbit IgG Fab specific for amyloid prefibrillar oligomers", Biochimica Et Biophysica Acta (BBA)—General Subjects, vol. 1820, No. 12, Dec. 1, 2012 (Dec. 1, 2012), pp. 1908-1914, XP055520611, 17 pages total.
Kenneth E. Bernstein et al., "Sequence of a cDNA Encoding Basilea Kappa Light Chains (K2 Isotype) Suggests a Possible Relationship of Protein Structure to Limited Expression", The Journal of Experimental Medicine Feb. 1, 1984, vol. 159, No. 2, Feb. 1, 1984 (Feb. 1, 1984), pp. 635-640, XP002786209, 6 pages total.
Earl F. Albone et al., "Generation of therapeutic immunoconjugates via Residue-Specific Conjugation Technology (RESPECT) utilizing a native cysteine in the light chain framework of *Oryctolagus cuniculus*", Cancer Biology & Therapy May 4, 2017, vol. 18, No. 5, May 4, 2017 (May 4, 2017), pp. 347-357, XP002786210, 11 pages total.
Communication pursuant to Article 94(3) EPC dated Jun. 3, 2020 in a counterpart European patent application No. 18187164.1.

* cited by examiner

SEQUENCE LISTING

<160> NUMBER OF SEQ ID NOS: 18

<210> SEQ ID NO 1
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 1
tgtgaagatg ctgccactta ttac                                         24

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 2
cgtcacgcca ctgatggtga                                              20

<210> SEQ ID NO 3
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 3
tgtacctaca gcctgagcag cac                                          23

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 4
gtcttcgggg ctctgcggtg                                              20

<210> SEQ ID NO 5
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 5
tgtgaagact tcgccacgta ttac                                              24

<210> SEQ ID NO 6
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 6
ctgcagagag ctgatcgtca gg                                                22

<210> SEQ ID NO 7
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 7
tgtacgtaca gcctgagttc cacc                                              24

<210> SEQ ID NO 8
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 8
gtcttttgaa tcttgttcgg tcacgg                                            26

<210> SEQ ID NO 9
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 9
tgtgaagatg ctgccactta ttac                                              24

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 10
ctccatgctg ctgattgtga g                                                 21

<210> SEQ ID NO 11
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 11
tgtgctgatg ctgcaccaac tgtatc                                            26

<210> SEQ ID NO 12
<211> LENGTH: 21
<212> TYPE: DNA

```
<213> ORGANISM: Artificial Sequence
<220> FEATURE:
<223> OTHER INFORMATION: Synthetic oligonucleotide primer

<400> SEQUENCE: 12
tctgatttcc agcttggtgc c                                              21

<210> SEQ ID NO 13
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 13
tgtacctaca gcatgagcag cac                                            23

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 14
gtctttgctg tcctgatcag                                                20

<210> SEQ ID NO 15
<211> LENGTH: 215
<212> TYPE: PRT
<213> ORGANISM: Oryctolagus cuniculus

<400> SEQUENCE: 15
```

Glu Leu Val Leu Thr Gln Thr Pro Ser Ser Val Ser Ala Ala Val Gly
1               5                   10                  15

Gly Thr Val Thr Ile Asn Cys Gln Ala Ser Gln Ser Val Ser Asn Leu
            20                  25                  30

Leu Ala Trp Tyr Gln Gln Lys Pro Gly Gln Pro Pro Lys Leu Leu Ile
        35                  40                  45

Tyr Gly Ala Ser Asn Leu Glu Ser Gly Val Pro Ser Arg Phe Arg Gly
    50                  55                  60

Ser Gly Ser Gly Thr Gln Phe Thr Leu Thr Ile Ser Gly Val Thr Ala
65                  70                  75                  80

Glu Asp Ala Ala Thr Tyr Tyr Cys Gln Ser Gly Tyr Tyr Ser Thr Gly
                85                  90                  95

Ala Ile Thr Phe Gly Lys Gly Thr Lys Leu Glu Ile Lys Arg Asp Pro
            100                 105                 110

Val Ala Pro Ser Val Leu Leu Phe Pro Pro Ser Lys Glu Glu Leu Thr
        115                 120                 125

Thr Gly Thr Ala Thr Ile Val Cys Val Ala Asn Lys Phe Tyr Pro Ser
    130                 135                 140

Asp Ile Thr Val Thr Trp Lys Val Asp Gly Thr Thr Gln Gln Ser Gly
145                 150                 155                 160

Ile Glu Asn Ser Lys Thr Pro Gln Ser Pro Glu Asp Asn Thr Tyr Ser
                165                 170                 175

Leu Ser Ser Thr Leu Ser Leu Thr Ser Ala Gln Tyr Asn Ser His Ser
            180                 185                 190

Val Tyr Thr Cys Glu Val Val Gln Gly Ser Ala Ser Pro Ile Val Gln
        195                 200                 205

```
Ser Phe Asn Arg Gly Asp Cys
    210             215
```

<210> SEQ ID NO 16
<211> LENGTH: 215
<212> TYPE: PRT
<213> ORGANISM: Artificial Sequence
<220> FEATURE:
<223> OTHER INFORMATION: Synthetic modified antibody sequence

<400> SEQUENCE: 16

```
Glu Leu Val Leu Thr Gln Thr Pro Ser Ser Val Ser Ala Ala Val Gly
1               5                   10                  15

Gly Thr Val Thr Ile Asn Cys Gln Ala Ser Gln Ser Val Ser Asn Leu
            20                  25                  30

Leu Ala Trp Tyr Gln Gln Lys Pro Gly Gln Pro Pro Lys Leu Leu Ile
        35                  40                  45

Tyr Gly Ala Ser Asn Leu Glu Ser Gly Val Pro Ser Arg Phe Arg Gly
    50                  55                  60

Ser Gly Ser Gly Thr Gln Phe Thr Leu Thr Ile Ser Gly Val Thr Cys
65                  70                  75                  80

Glu Asp Ala Ala Thr Tyr Tyr Cys Gln Ser Gly Tyr Tyr Ser Thr Gly
                85                  90                  95

Ala Ile Thr Phe Gly Lys Gly Thr Lys Leu Glu Ile Lys Arg Asp Pro
            100                 105                 110

Val Ala Pro Ser Val Leu Leu Phe Pro Pro Ser Lys Glu Glu Leu Thr
        115                 120                 125

Thr Gly Thr Ala Thr Ile Val Cys Val Ala Asn Lys Phe Tyr Pro Ser
130                 135                 140

Asp Ile Thr Val Thr Trp Lys Val Asp Gly Thr Thr Gln Gln Ser Gly
145                 150                 155                 160

Ile Glu Asn Ser Lys Thr Pro Gln Ser Pro Glu Asp Cys Thr Tyr Ser
                165                 170                 175

Leu Ser Ser Thr Leu Ser Leu Thr Ser Ala Gln Tyr Asn Ser His Ser
            180                 185                 190

Val Tyr Thr Cys Glu Val Val Gln Gly Ser Ala Ser Pro Ile Val Gln
        195                 200                 205

Ser Phe Asn Arg Gly Asp Cys
    210             215
```

<210> SEQ ID NO 17
<211> LENGTH: 214
<212> TYPE: PRT
<213> ORGANISM: Homo sapiens

<400> SEQUENCE: 17

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
```

```
                    85                  90                  95
Thr Phe Gly Gln Gly Thr Lys Val Glu Ile Lys Arg Thr Val Ala Ala
                100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
                180                 185                 190
Ala Cys Glu Val Thr His Gln Gly Leu Ser Leu Pro Val Thr Lys Ser
            195                 200                 205
Phe Asn Arg Gly Glu Cys
    210
```

<210> SEQ ID NO 18
<211> LENGTH: 214
<212> TYPE: PRT
<213> ORGANISM: Artificial Sequence
<220> FEATURE:
<223> OTHER INFORMATION: Synthetic modified antibody sequence

<400> SEQUENCE: 18

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Asn Thr Ala
                20                  25                  30
Val Ala Trp Tyr Gln Gln Lys Pro Gly Lys Ala Pro Lys Leu Leu Ile
            35                  40                  45
Tyr Ser Ala Ser Phe Leu Tyr Ser Gly Val Pro Ser Arg Phe Ser Gly
        50                  55                  60
Ser Arg Ser Gly Thr Asp Phe Thr Leu Thr Ile Ser Ser Leu Gln Cys
65                  70                  75                  80
Glu Asp Phe Ala Thr Tyr Tyr Cys Gln Gln His Tyr Thr Thr Pro Pro
                85                  90                  95
Thr Phe Gly Gln Gly Thr Lys Val Glu Ile Lys Arg Thr Val Ala Ala
                100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Cys Thr Tyr Ser Leu Ser
                165                 170                 175
Ser Thr Leu Thr Leu Ser Lys Ala Asp Tyr Glu Lys His Lys Val Tyr
                180                 185                 190
Ala Cys Glu Val Thr His Gln Gly Leu Ser Leu Pro Val Thr Lys Ser
            195                 200                 205
Phe Asn Arg Gly Glu Cys
    210
```

METHOD FOR PRODUCING ANTIBODY

CROSS REFERENCE TO RELATED APPLICATIONS

This application claims priority from prior Japanese Patent Application No. 2017-151866, filed on Aug. 4, 2017, entitled "ANTIBODY, METHOD FOR PRODUCING SAME, AND METHOD FOR IMPROVING THERMAL STABILITY OF ANTIBODY", the entire contents of which are incorporated herein by reference.

TECHNICAL FIELD

The present invention relates to an antibody, and a method for producing the antibody. The present invention also relates to a method for improving the thermal stability of an antibody.

BACKGROUND

A technique has been heretofore known in which a mutation is introduced into an amino acid sequence of an antibody to modify the affinity of the antibody for an antigen. However, while the affinity for the antigen may be modified as desired by introduction of the mutation, the thermal stability of the antibody may be deteriorated. The thermal stability of an antibody correlates with the storage stability and aggregation resistance of the antibody, and is therefore used as one of indices in development of antibody drugs.

The thermal stability of an antibody is often affected by the molecular structure of the antibody. Regarding the molecular structure of an antibody, for example, Arai H. et al., "Crystal structure of a conformation-dependent rabbit IgG Fab specific for amyloid prefibrillar oligomers, Biochim Biophys Acta. vol. 1820, p. 1908-1914, 2012" reveals that by crystallization analysis of an antigen-binding fragment (Fab) of a rabbit IgG antibody, a light chain of the rabbit antibody is found to have a characteristic disulfide bond. More specifically, Arai H. et al., "Crystal structure of a conformation-dependent rabbit IgG Fab specific for amyloid prefibrillar oligomers, Biochim Biophys Acta. Vol. 1820, p. 1908-1914, 2012" suggests that at positions 80 and 171 based on the Kabat method in a light chain of a rabbit antibody, two cysteine residues absent in a human antibody and a mouse antibody are present, and the disulfide bond specific to the rabbit antibody is formed between these cysteine residues.

In general, a disulfide bond is known to affect the structure of protein molecules. However, Arai H. et al., "Crystal structure of a conformation-dependent rabbit IgG Fab specific for amyloid prefibrillar oligomers, Biochim Biophys Acta. Vol. 1820, p. 1908-1914, 2012" suggests that the Fab of a rabbit antibody is extremely similar in structure to the Fab of a human-rabbit chimeric antibody, and the Fab of the rabbit antibody is not different in overall structure and stability from the Fab of the chimeric antibody. As described above, cysteine residues are not present at positions 80 and 171 based on the Kabat method in a light chain of a human antibody, and therefore a disulfide bond specific to a rabbit antibody is not present in the human-rabbit chimeric antibody in Arai H. et al., "Crystal structure of a conformation-dependent rabbit IgG Fab specific for amyloid prefibrillar oligomers, Biochim Biophys Acta. vol. 1820, p. 1908-1914, 2012". That is, Arai H. et al., "Crystal structure of a conformation-dependent rabbit IgG Fab specific for amyloid prefibrillar oligomers, Biochim Biophys Acta. vol. 1820, p. 1908-1914, 2012" indicates that the disulfide bond specific to the rabbit antibody does not contribute to the structure and stability of an antibody.

SUMMARY

The scope of the present invention is defined solely by the appended claims, and is not affected to any degree by the statements within this summary.

Since the thermal stability of an antibody is a factor related to the quality of the antibody like storage stability and aggregation resistance as described above, establishment of a technique for improving the thermal stability of the antibody is desired. In general, a disulfide bond in a protein molecule may be involved in thermal stability, and therefore the present inventors have paid attention to a disulfide bond specific to a rabbit antibody. The present inventors have measured the thermal stability of each of various rabbit antibodies, and resultantly found that surprisingly, contrary to the indication by Arai H. et al., "Crystal structure of a conformation-dependent rabbit IgG Fab specific for amyloid prefibrillar oligomers, Biochim Biophys Acta. Vol. 1820, p. 1908-1914, 2012", a disulfide bond specific to a rabbit antibody contributes to improvement of thermal stability. The present inventors have also found that rabbit antibodies include antibodies having no cysteine residues at positions 80 and 171 of a light chain, and that when the 80th and 171th amino acid residues of the light chain of the antibody are substituted with cysteine, thermal stability is improved. The present inventors have also found that when an antibody derived from a mammal other than a rabbit is subjected to similar substitution, the thermal stability of the antibody is improved.

A first aspect of the present invention is to provide an antibody in which the 80th amino acid residue in a variable region based on the Kabat method and the 171th amino acid residue (171th amino acid residue in the EU index) in a constant region based on the Kabat method are substituted with cysteine in an antibody in which the 80th amino acid residue in the variable region and the 171th amino acid residue in the constant region are not cysteine.

A second aspect of the present invention is to provide a method for producing an antibody, the method including the steps of: substituting the 80th amino acid residue in a variable region based on the Kabat method and the 171th amino acid residue in a constant region based on the Kabat method with cysteine in an antibody in which the 80th amino acid residue in the variable region and the 171th amino acid residue in the constant region are not cysteine; and recovering the antibody obtained in the substitution step.

A third aspect of the present invention is to provide a method for improving the thermal stability, the method including substituting the 80th amino acid residue in a variable region based on the Kabat method and the 171th amino acid residue in a constant region based on the Kabat method with cysteine in an antibody in which the 80th amino acid residue in the variable region and the 171th amino acid residue in the constant region are not cysteine.

DETAILED DESCRIPTION OF THE PREFERRED EMBODIMENTS

[1. Antibody Having Improved Thermal Stability]

Figure 1:
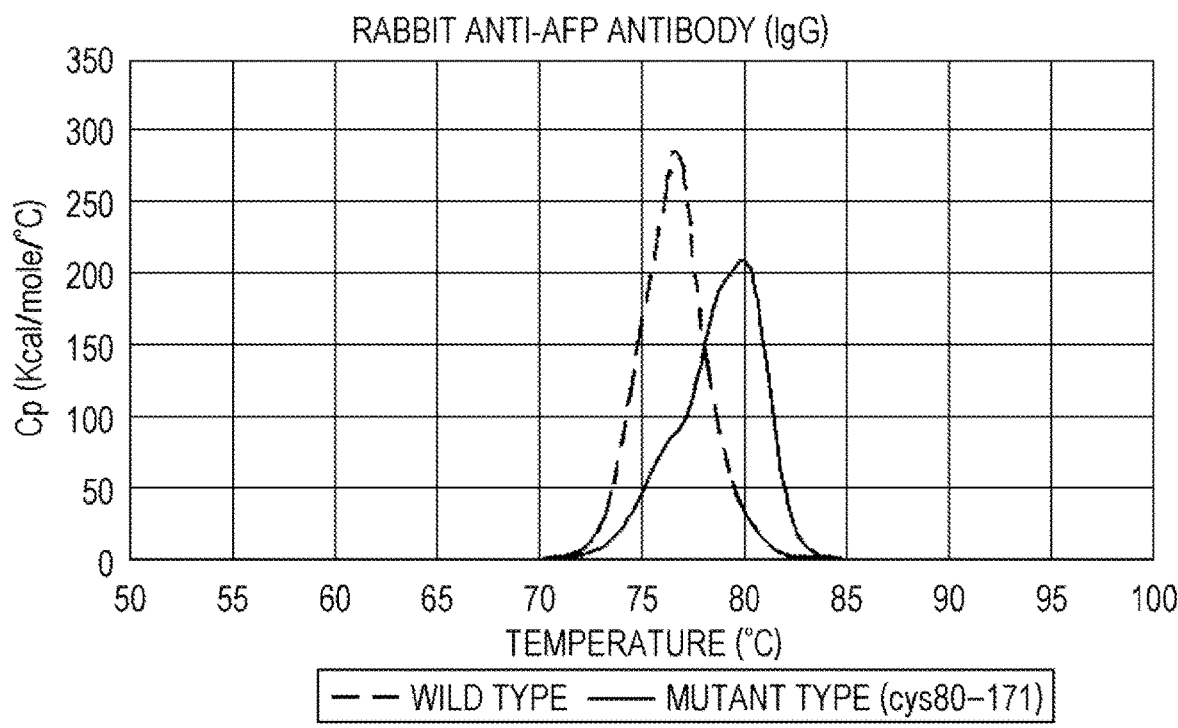
FIG. 1 is a graph showing analytical peaks when the thermal stability of a wild type and a mutant type (cys 80-171) of a rabbit anti-alpha fetoprotein (AFP) antibody is measured by a differential scanning calorimeter (DSC). The "mutant type (cys 80-171)" refers to an antibody in which the 80th amino acid residue in a variable region and the 171th amino acid residue in a constant region in the wild-type antibody are substituted with cysteine. Numbering of amino acid residues in the variable region and the constant region is based on the Kabat method.
Figure 2:
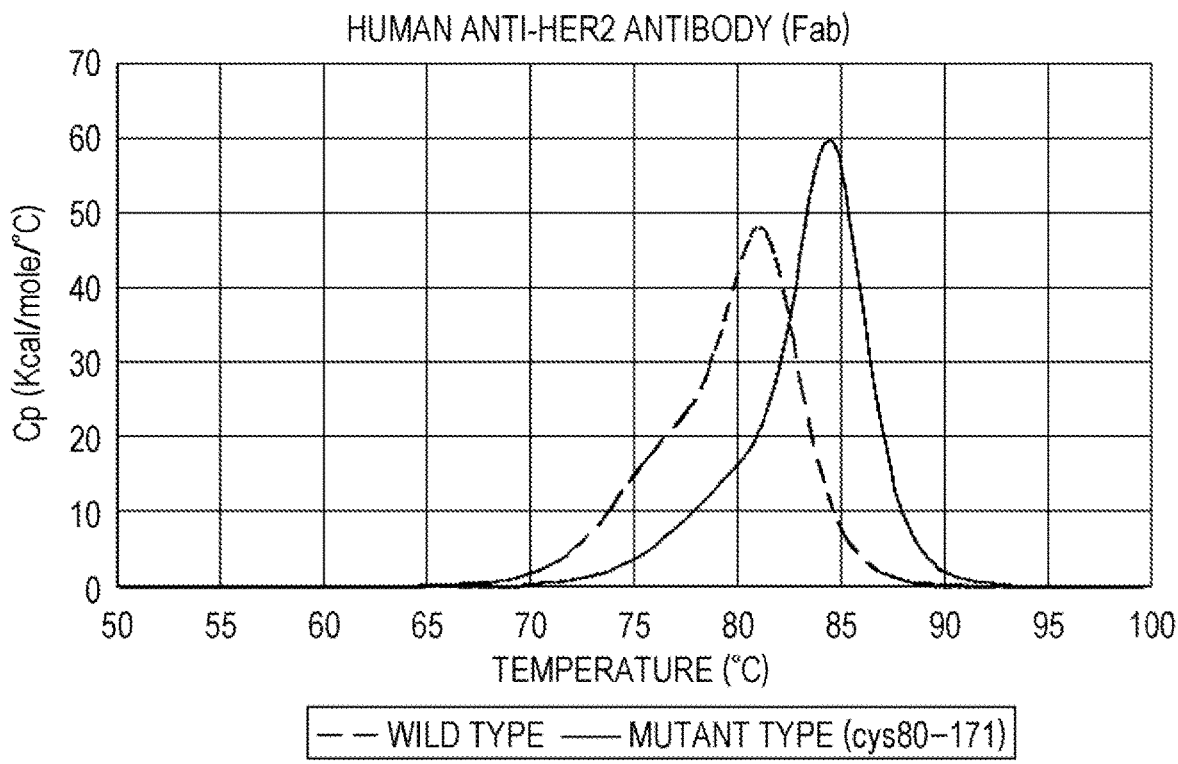
FIG. 2 is a graph showing analytical peaks when the thermal stability of a wild type and a mutant type (cys 80-171) of a human anti-human epidermal growth factor receptor type 2 (HER2) antibody (Fab) is measured by DSC.
Figure 3A:
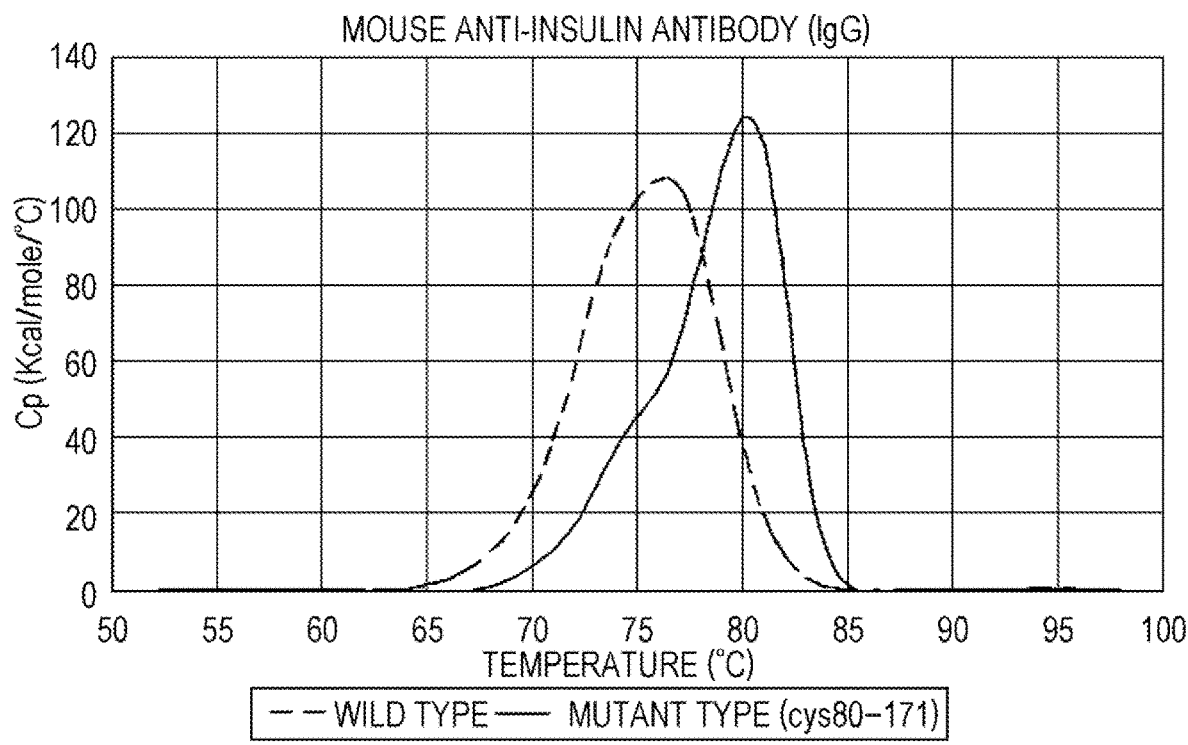
FIG. 3A is a graph showing analytical peaks when the thermal stability of a wild type and a mutant type (cys 80-171) of a mouse anti-insulin antibody is measured by DSC.
Figure 3B:
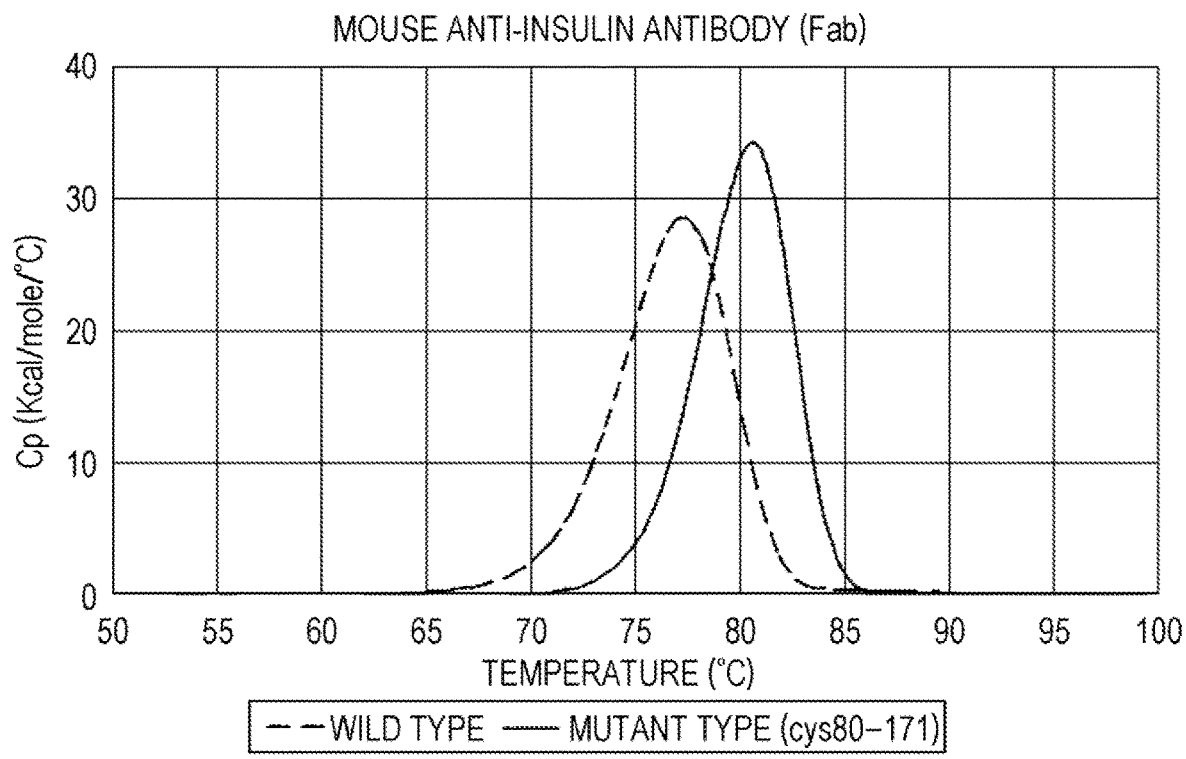
FIG. 3B is a graph showing analytical peaks when the thermal stability of a wild type and a mutant type (cys 80-171) of a mouse anti-insulin antibody (Fab) is measured by DSC.
Figure 3C:
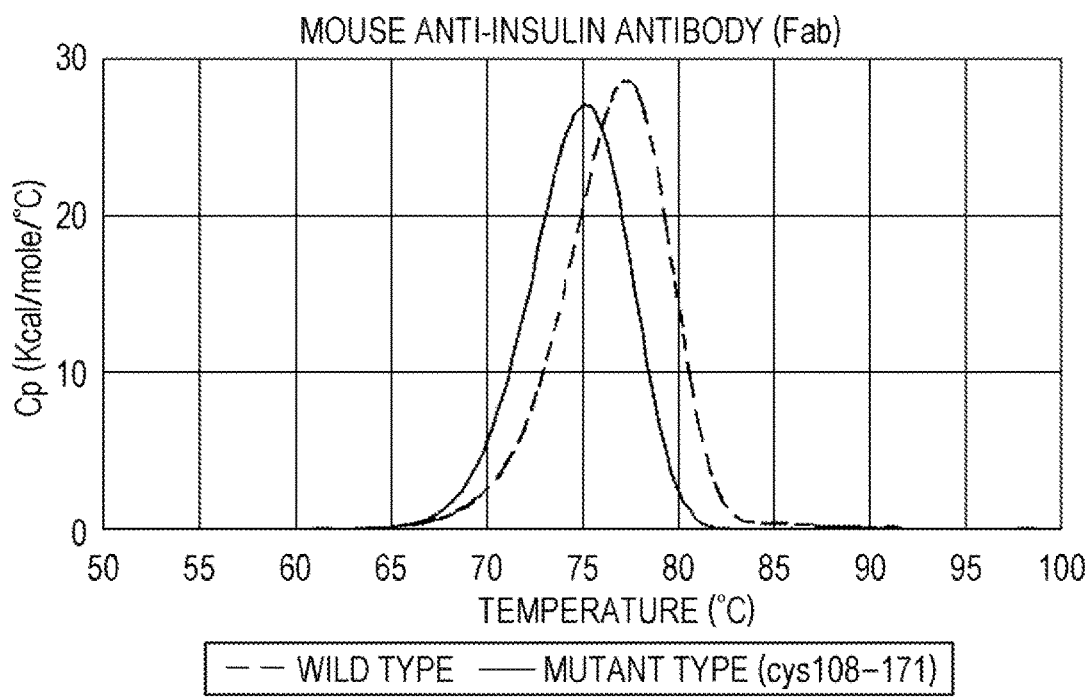
FIG. 3C is a graph showing analytical peaks when the thermal stability of a wild type and a mutant type (cys 108-171) of a mouse anti-insulin antibody (Fab) is measured by DSC. The "mutant type (cys 108-171)" refers to an antibody in which the 108th amino acid residue in a variable region and the 171th amino acid residue in a constant region in the wild-type antibody are substituted with cysteine.

In an antibody of an embodiment, the 80th amino acid residue in a variable region based on the Kabat method and the 171th amino acid residue in a constant region based on the Kabat method are substituted with cysteine in an antibody in which the 80th amino acid residue in the variable region and the 171th amino acid residue in the constant region are not cysteine. As a result of the substitution of amino acid residues, the thermal stability of the antibody is improved as compared to an original antibody before the substitution is performed. That is, the antibody of this embodiment is an antibody artificially modified so as to improve thermal stability (hereinafter, also referred to as a "modified antibody").

In this specification, the phrase "based on the Kabat method" means that an amino acid residue in a variable region of an antibody is numbered in accordance with the numbering scheme by Kabat et al. (see Kabat E. A. et al, Sequences of Proteins of Immunological Interest, 5th ed. Public Health Service, National Institutes of Health, Bethesda, Md. (1991), NIH Publication No. 91-3242), and an amino acid residue in a constant region of an antibody is numbered in accordance with the EU index by Kabat et al. The EU index is described in the above-mentioned document by Kabat et al.

Hereinafter, the antibody in which the 80th amino acid residue in the variable region based on the Kabat method and the 171th amino acid residue in the constant region based on the Kabat method are not cysteine is also referred to as an "original antibody". Hereinafter, the 80th amino acid residue in the variable region based on the Kabat method is also referred to simply as the "80th amino acid residue", and the 171th amino acid residue in the constant region based on the Kabat method is also referred to simply as the "171th amino acid residue". Each of the 80th and 171th amino acid residues in the original antibody may be any amino acid residue except cysteine.

The 80th amino acid residue in the variable region based on the Kabat method and the 171th amino acid residue in the constant region based on the Kabat method are present in both a light chain and a heavy chain. In this embodiment, the original antibody may be an antibody in which the amino acid residue at the above-mentioned position in one or both of the light chain and the heavy chain is not cysteine. In a preferred embodiment, the original antibody is an antibody in which the 80th amino acid residue in the light chain and the 171th amino acid residue in the light chain are not cysteine. It is considered that when the 80th and 171th amino acid residues in the light chain are substituted with cysteine, a disulfide bond is formed between these cysteine residues, i.e. between the variable region of the light chain and the constant region of the light chain. This disulfide bond corresponds to a disulfide bond specific to the above-mentioned rabbit antibody.

The original antibody may be an antibody that recognizes any antigen. The original antibody may be a natural antibody or an artificially produced antibody as long as the 80th and 171th amino acid residues are not cysteine. Examples of the artificially produced antibody include an antibody with a mutation (substitution, addition or deletion of an amino acid residue) introduced into an amino acid sequence of a natural antibody, a chimeric antibody, and a humanized antibody.

The original antibody may be an antibody derived from any animal as long as the 80th and 171th amino acid residues are not cysteine. Such animals are preferably mammals such as, for example, humans, mice, rabbits, rats, pigs, sheep, goats, camels, cows and horses. Among them, humans, mice and rabbits are preferable. The modified antibody in this embodiment is derived from an animal having an antibody identical to the original antibody.

In a preferred embodiment, the original antibody is an antibody, the gene base sequence of which is known or identifiable. Specifically, the original antibody is an antibody, the antibody gene base sequence of which is disclosed in a known database, or an antibody for which the hybridoma producing the antibody is available. Examples of the database include GenBank provided by National Center for Biotechnology Information (NCBI). When there is a hybridoma producing the original antibody, the antibody gene base sequence can be obtained by acquiring an antibody gene from the hybridoma by a known method, and sequencing the base sequence of the antibody gene.

The modified antibody in this embodiment has improved thermal stability as compared to the original antibody. The thermal stability of an antibody can be generally evaluated by measuring the amount or ratio of the antibody degenerated with thermal stress. The measurement method itself is known in the art, and is, for example, measurement by a differential scanning calorimeter (DSC), a CD spectrum, a fluorescence spectrum or a Fourier transform infrared spectrophotometer (FTIR). In this embodiment, it is preferable that the thermal stability of an antibody is evaluated by information obtained from measurement by DSC. The information may be, for example, Tm (temperature at which the heat capacity is the maximum), or an analytical peak itself.

In this embodiment, the Tm value of the modified antibody measured by DSC is higher than the Tm value of the original antibody. For example, the Tm value of the modified antibody as measured by DSC is higher than the Tm value of the original antibody by at least about 1° C., preferably at least about 2° C., more preferably at least about 3° C.

Substitution of the 80th and 171th amino acid residues in the original antibody with cysteine has little influence on affinity for an antigen. Thus, the modified antibody in this embodiment binds to an antigen identical to one to which the original antibody binds, and the affinity for the antigen is comparable to that of the original antibody. The affinity of an antibody for an antigen may be evaluated by an immunological measurement method such as the ELISA method, or evaluated by kinetic parameters (binding rate constant, dissociation rate constant and dissociation constant) in an antigen-antibody reaction. The kinetic parameters can be acquired by a surface plasmon resonance (SPR) technique.

In this embodiment, the class of each of the original antibody and the modified antibody may be any of IgG, IgA, IgM, IgD and IgE, but is preferably IgG. The subclass of IgG is not particularly limited, and may be any of IgG1, IgG2, IgG3 and IgG4. In this embodiment, the type of the light chain of each of the original antibody and the modified antibody is preferably a kappa (κ) chain.

In this embodiment, the original antibody may be in the form of an antibody fragment as long as the original antibody has the 80th and 171th amino acid residues which are substituted with cysteine. The modified antibody may be in the form of an antibody fragment as long as the modified antibody contains the 80th and 171th sites substituted with cysteine. Examples of the antibody fragment include Fab, F(ab')2, Fab' and Fd. Among them, Fab is particularly preferable.

The method of use of the modified antibody in this embodiment is not particularly different from the method of use of the original antibody. As with the original antibody, the modified antibody can be used for various tests and studies, antibody drugs or the like. The modified antibody in this embodiment may be modified with a labeling substance etc. known in the art.

[2. Method for Producing Antibody]

With a method for producing an antibody according to this embodiment (hereinafter, also referred to simply as a "production method"), the above-described modified antibody in this embodiment can be obtained. In the production method according this embodiment, first the 80th amino acid residue in a variable region based on the Kabat method and the 171th amino acid residue in a constant region based on the Kabat method are substituted with cysteine in an antibody in which the 80th amino acid residue in the variable region and the 171th amino acid residue in the constant region are not cysteine.

In the production method according to this embodiment, the antibody in which the 80th amino acid residue in the variable region based on the Kabat method and the 171th amino acid residue in the constant region based on the Kabat method are not cysteine is identical to the above-described "original antibody". Substitution of the 80th and 171th amino acid residues in the original antibody with cysteine can be performed by a known method such as a DNA recombination technique or other molecular biological technique. For example, when there is a hybridoma that produces the original antibody, a polynucleotide encoding a light chain and a polynucleotide encoding a heavy chain are synthesized, respectively, by a reverse transcription reaction and RACE (Rapid Amplification of cDNA ends) method using RNA extracted from the hybridoma as shown in Example 1 described later. For example, when the 80th and 171th amino acid residues in the light chain of the original antibody are substituted with cysteine, polynucleotide encoding a light chain having cysteine at positions 80 and 171 can be obtained by amplifying the polynucleotide encoding a light chain by the PCR method using a primer for substituting the 80th and 171th amino acid residues. The obtained polynucleotide is incorporated into an expression vector known in the art together with a polynucleotide encoding the heavy chain of the original antibody to obtain an expression vector containing a polynucleotide encoding the modified antibody in this embodiment.

The polynucleotide encoding a light chain and the polynucleotide encoding a heavy chain may be incorporated into one expression vector, or separately incorporated into two expression vectors. The type of the expression vector is not particularly limited, and may be an expression vector for mammalian cells or an expression vector for E. coli. By transducing or transfecting the obtained expression vector into appropriate host cells (e.g. mammalian cells or E. coli), a modified antibody can be obtained.

When a hybridoma that produces the original antibody is not present, an antibody-producing hybridoma may be prepared by a known method such as a method described in, for example, Kohler and Milstein, Nature, vol. 256, p. 495-497, 1975. Alternatively, RNA acquired from peripheral blood or spleen of an animal such as a mouse or rabbit immunized with a predetermined antigen may be used. When RNA acquired from peripheral blood or spleen is used, cDNA may be synthesized from the RNA, followed by preparing a Fab phage library from the obtained cDNA as shown in a reference example below. Using this library, a polynucleotide encoding Fab as the original antibody can be acquired by a phage display method or the like. By amplifying the obtained polynucleotide by the above-mentioned PCR method, Fab in which the 80th and 171th amino acid residues are substituted with cysteine can be obtained as the modified antibody in this embodiment.

Next, in the production method according to this embodiment, the antibody obtained in the above-mentioned substitution step is recovered. For example, a host cell that expresses the modified antibody is dissolved in a solution containing an appropriate solubilizer, so that the antibody is liberated in the solution. When the host cell secretes the modified antibody into a medium, a culture supernatant is recovered. The liberated antibody can be recovered by a method known in the art such as affinity chromatography. For example, when the produced modified antibody is IgG, the antibody can be recovered by affinity chromatography using Protein A or G. If necessary, the recovered antibody may be purified by a method known in the art such as gel filtration.

Details of the antibody obtained by the production method according to this embodiment are the same as those described for the above-mentioned modified antibody. The antibody obtained by the production method according to this embodiment has improved thermal stability as compared to the original antibody. Details of the thermal stability of the antibody and the method for measuring the thermal stability are the same as described for the modified antibody in this embodiment.

As described above, substitution of the 80th and 171th amino acid residues in the original antibody with cysteine has little influence on affinity for an antigen. Thus, the modified antibody obtained by the production method according to this embodiment binds to an antigen identical to one to which the original antibody binds, and the affinity for the antigen is comparable to that of the original antibody. Details of the affinity of the antibody for an antigen and the method for evaluating the affinity are the same as described for the modified antibody in this embodiment.

[3. Method for Improving Thermal Stability of Antibody]

With a method for improving the thermal stability of an antibody according to this embodiment (hereinafter, also referred to simply as a "method"), it is possible to improve the thermal stability of an antibody in which the 80th amino acid residue in a variable region based on the Kabat method and the 171th amino acid residue in a constant region based on the Kabat method are not cysteine. The antibody targeted by the method according to this embodiment is identical to the "original antibody" described above. In the method according to this embodiment, the 80th amino acid residue in the variable region based on the Kabat method and the 171th amino acid residue in the constant region based on the Kabat method in the original antibody are substituted with cysteine to improve thermal stability.

Substitution of the 80th and 171th amino acid residues in the original antibody can be performed by a known method such as a DNA recombination technique or other molecular biological technique as described above. For example, when there is a hybridoma that produces the original antibody, an expression vector containing a polynucleotide encoding the modified antibody can be acquired in the same manner as described for the production method according to this embodiment. The obtained expression vector can be transduced or transfected into an appropriate host cell to acquire the host cell expressing the antibody.

It is considered that in the method according to this embodiment, introduction of cysteine into the 80th and 171th amino acid residues in the original antibody forms a disulfide bond between the cysteine residues, leading to improvement of the thermal stability of the antibody. As described above, substitution of the 80th and 171th amino acid residues in the original antibody with cysteine has little influence on affinity for an antigen. Thus, when the method according to this embodiment is applied to a mutant antibody in which introduction of a mutant has improved affinity for an antigen, but has deteriorated thermal stability, it is possible to improve the thermal stability while maintaining the affinity of the antibody to an antigen.

The scope of the present disclosure includes an isolated and purified polynucleotide encoding the antibody having improved thermal stability in this embodiment, or a fragment of the antibody. Preferably, the isolated and purified polynucleotide encoding a fragment of the modified antibody in this embodiment encodes a variable region containing cysteine at the position 80 based on the Kabat method and a constant region containing cysteine at the position 171 based on the Kabat method. The scope of the present disclosure also includes a vector containing the above-mentioned polynucleotide. The vector is a polynucleotide structure designed for transduction or transfection. The type of the vector is not particularly limited, and the vector can be appropriately selected from vectors known in the art, such as expression vectors, cloning vectors and viral vectors. The scope of the present disclosure also includes a host cell containing the vector. The type of the host cell is not particularly limited, and the host cell can be appropriately selected from eukaryotic cells, prokaryotic cells and mammalian cells.

Hereinafter, the present disclosure will be described more in detail by way of examples, but the present disclosure is not limited to these examples.

EXAMPLES

Reference Example: Relationship Between Disulfide Bond and Thermal Stability in Rabbit Fab As described above, Arai H. et al., "Crystal structure of a conformation-dependent rabbit IgG Fab specific for amyloid prefibrillar oligomers, Biochim Biophys Acta. Vol. 1820, p. 1908-1914, 2012" indicates that a disulfide bond (formed between the 80th and 171th cysteine residues of the light chain) specific to a rabbit antibody does not contribute to stability. However, since the disulfide bond in the protein molecule may be involved in thermal stability, the inventors actually measured the thermal stability of Fab as a rabbit antibody.

(1) Acquisition of Rabbit Fab Clone

Lymphocytes were acquired from peripheral blood of a rabbit immunized with AFP, and mRNA was extracted from the lymphocytes to synthesize cDNA. Using a known primer for cloning an antibody gene, the obtained cDNA was amplified to prepare a Fab phage library. Using the obtained library, three Fab clones of a rabbit anti-AFP antibody were obtained by a known Fab phage display method and bio-panning (see Lang I M, Barbas C F 3rd, Schleef R R., Recombinant rabbit Fab with binding activity to type-1 plasminogen activator inhibitor derived from a phage-display library against human alpha-granules, (1996) Gene 172(2):295-8 and Philippa M. O'Brien, Robert Aitken, Antibody Phage Display, (2002) Methods in Molecular Biology Volume No. 178). These clones are hereinafter referred to as "A1", "2-2-37" and "C3".

The number of disulfide bonds formed in the Fab molecule was examined on the basis of the amino acid sequence of each Fab clone. Clone A1 was found to be Fab having six disulfide bonds (hereinafter, also referred to as a "six-SS type") as with a human antibody and a mouse antibody. The Fab of six-SS type has one disulfide bond in the variable region of the light chain, one disulfide bond in the variable region of the heavy chain, one disulfide bond in the constant region of the light chain, two disulfide bonds in the constant region of the heavy chain, and one disulfide bond between the constant region of the light chain and the constant region of the heavy chain.

Clone 2-2-37 was found to be Fab having seven disulfide bonds (hereinafter, also referred to as a "seven-SS type"). Clone 2-2-37 has cysteine residues at position 80 in the variable region of the light chain and position 171 in the constant region of the light chain as with the rabbit Fab described in Arai H. et al., Crystal structure of a conformation-dependent rabbit IgG Fab specific for amyloid prefibrillar oligomers, Biochim Biophys Acta. Vol. 1820, p. 1908-1914, 2012. That is, the Fab of seven-SS type has a disulfide bond between the variable region of the light chain and the constant region of the light chain in addition to six disulfide bonds of the Fab of six-SS type.

Clone C3 was found to be Fab having eight disulfide bonds (hereinafter, also referred to as an "eight-SS type"). The Fab of eight-SS type has a disulfide bond in the variable region of the heavy chain in addition to seven disulfide bonds of the Fab of seven-SS type.

(2) Measurement of Thermal Stability

By gel filtration, a solvent of a solution containing each Fab clone obtained was replaced by a buffer (phosphate buffered saline: PBS) to be used for measurement with a differential scanning calorimeter (DSC). Conditions for gel filtration are as follows.

[Condition for Gel Filtration]
Buffer: PBS (pH 7.4)
Column used: Superdex® 200 Increase 10/300 (GE Healthcare)
Column volume (CV): 24 mL
Sample volume: 500 μL
Flow rate: 1.0 mL/min
Elution amount: 1.5 CV
Fraction volume: 500 μL The fraction containing each Fab clone was diluted with PBS to prepare a sample (final concentration: 5 μM). The Tm value of each Fab clone was measured using MicroCal PEAQ-DSC (Malvern Instruments Ltd.). Measurement conditions are as follows.

[DSC Measurement Conditions]
Sample amount: 400 μL
Measurement range: 30° C. to 100° C.
Temperature elevation rate: 1° C./min (3) Results The Tm values of the Fab clones, which were obtained by DSC measurement, are shown in Table 1.

TABLE 1

| Clone | Type | Tm (° C.) |
|---|---|---|
| A1 | Six-SS type | 74 |
| 2-2-37 | Seven-SS type | 81 |
| C3 | Eight-SS type | 81 |

Clones 2-2-37 and C3 each had a Tm value higher by 7° C. than that of clone A1. Clones 2-2-37 and C3 had the same Tm value. These results showed that the disulfide bond between the 80th cysteine residue in the light chain variable region and the 171th cysteine residue in the constant region of the light chain in the Fab of seven-SS type contributed to thermal stability.

Example 1: Preparation of Modified Antibody

Whether or not introduction of a mutation into each of a rabbit antibody (six-SS type), a human antibody and a mouse antibody so as to form a disulfide bond specific to a rabbit antibody of seven-SS type improved the thermal stability of each antibody was examined.

(1) Acquisition of Gene of Each Antibody (1.1) Acquisition of Gene of Rabbit Antibody The gene of the Fab clone A1 of the rabbit anti-AFP antibody, which was obtained in the reference example, was incorporated into a plasmid DNA containing a gene encoding a Fc region of the rabbit antibody, thereby acquiring a plasmid DNA containing the gene of the rabbit anti-AFP antibody.

(1.2) Acquisition of Gene of Human Antibody

A gene of a human anti-HER2 monoclonal antibody (trastuzumab) was synthesized by GenScript Japan Inc. on commission, so that a plasmid DNA containing a gene of a human anti-HER2 antibody was acquired.

(1.3) Acquisition of Gene of Mouse Antibody

A mouse anti-insulin antibody gene was acquired in the following manner. [Reagents]
ISOGEN (NIPPON GENE CO., LTD.)
SMARTer® RACE 5'/3' Kit (Clontech Laboratories, Inc.)
10× A-attachment mix (TOYOBO CO., LTD.)
pcDNA™ 3.4 TOPO® TA Cloning Kit (Thermo Fisher Scientific Inc.)
Competent high DH5α (TOYOBO CO., LTD.)
QIAprep® Spin Miniprep Kit (QIAGEN)
KOD plus neo (TOYOBO CO., LTD.)
Ligation high ver. 2 (TOYOBO CO., LTD.)

(i) Extraction of Total RNA from Antibody-Producing Hybridoma

Using human insulin as an antigen, a hybridoma producing a mouse anti-human insulin antibody was prepared by the method described in Kohler and Milstein, Nature, vol. 256, p. 495-497, 1975. A culture of the hybridoma (10 mL) was centrifuged at 1000 rpm for 5 minutes, and the supernatant was removed. The obtained cells were dissolved in ISOGEN (1 mL), and left standing at room temperature for 5 minutes. Chloroform (200 μL) was added thereto, and the mixture was stirred for 15 seconds, and then left standing at room temperature for 3 minutes. This was centrifuged at 12000×G for 10 minutes at 4° C., and an aqueous phase containing RNA (500 μL) was recovered. Isopropanol (500 μL) was added to and mixed with the recovered aqueous phase. The resulting mixture was left standing at room temperature for 5 minutes, and then centrifuged at 12000×G for 10 minutes at 4° C. The supernatant was removed, 70% ethanol (1 mL) was added to the resulting precipitate (total RNA), and the mixture was centrifuged at 7500×G for 10 minutes at 4° C. The supernatant was removed, and RNA was air-dried, and dissolved in RNase-free water (20 μL).

(ii) Synthesis of cDNA

Using each total RNAs obtained in (i) above, a RNA sample having the following composition was prepared.

[RNA Sample]

| Total RNA (500 ng/μL) | 1 μL |
|---|---|
| RT primer | 1 μL |
| deionized water | 1.75 μL |
| total | 3.75 μL |

The prepared RNA sample was heated at 72° C. for 3 minutes, and then incubated at 42° C. for 2 minutes. 12 μM SMARTer® IIA oligonucleotide (1 μL) was added to the RNA sample to prepare a sample for synthesis of cDNA. Using the sample for synthesis of cDNA, a reverse transcription reaction solution having the following composition was prepared.

[Reverse Transcription Reaction Solution]

| 5× First-Strand buffer | 2 μL |
|---|---|
| 20 mM DTT | 1 μL |
| 10 mM dNTP mix | 1 μL |
| RNAase inhibitor | 0.25 μL |
| SMARTScribe™ RT (100 U/μL) | 1 μL |
| sample for synthesis of cDNA | 4.75 μL |
| total | 10 μL |

The prepared reverse transcription reaction solution was reacted at 42° C. for 90 minutes. The reaction solution was heated at 70° C. for 10 minutes, and tricine-EDTA (50 μL) was added. Using the obtained solution as a cDNA sample, a 5' RACE reaction solution having the following composition was prepared.

[5' RACE Reaction Solution]

| 10× PCR buffer | 5 μL |
|---|---|
| dNTP mix | 5 μL |
| 25 mM Mg$_2$SO$_4$ | 3.5 μL |

| | |
|---|---|
| cDNA sample | 2.5 µL |
| 10x Universal Primer Mix | 5 µL |
| 3'-primer | 1 µL |
| KOD plus neo (1 U/µL) | 1 µL |
| purified water | 27 µL |
| total | 50 µL |

The prepared 5' RACE reaction solution was subjected to a RACE reaction under the following reaction conditions. The "Y" described below is 90 seconds for the light chain and 150 seconds for the heavy chain.
[Reaction Conditions]
30 cycles each including 2 minutes at 94° C., 10 seconds at 98° C., 30 seconds at 50° C. and Y seconds at 68° C., and 3 minutes at 68° C.

Using the 5' RACE product obtained in the above-mentioned reaction, a solution having the following composition was prepared. The solution was reacted at 60° C. for 30 minutes to add adenine to the end of the 5' RACE product.

| | |
|---|---|
| 5' RACE product | 9 µL |
| 10x A-attachment mix | 1 µL |
| total | 10 µL |

Using the obtained adenine addition product and pcDNA™ 3.4 TOPO® TA Cloning Kit, a TA cloning reaction solution having the following composition was prepared. The reaction solution was incubated at room temperature for 10 minutes to clone the adenine addition product into pCDNA™ 3.4.
[TA Cloning Reaction Solution]

| | |
|---|---|
| Adenine addition product | 4 µL |
| salt solution | 1 µL |
| pCDNA™ 3.4 | 1 µL |
| total | 6 µL |

(iii) Examination of Transformation, Plasmid Extraction and Sequence

The TA cloning sample (3 µL) obtained in (ii) above was added to DH5α (30 µL), and the mixture was left standing on ice for 30 minutes, and then heated at 42° C. for 45 seconds to give a heat shock. The mixture was left standing on ice again for 2 minutes, and totally applied to an ampicillin-containing LB plate. The plate was incubated at 37° C. for 16 hours. A single colony on the plate was taken in an ampicillin-containing LB liquid medium, and subjected to shaking culture (250 rpm) at 37° C. for 16 hours. The culture was centrifuged at 5000×G for 5 minutes to recover an *E. coli* transformant. A plasmid was extracted from the recovered *E. coli* using QIAprep® Spin Miniprep Kit. Specific operations were carried out in accordance with the manual attached to the kit. The base sequence of the obtained plasmid was identified using a pCDNA™ 3.4 vector primer. In this way, a plasmid DNA containing a gene of a mouse anti-insulin antibody was obtained.

(2) Acquisition of Mutant-Type Gene of Each Antibody
(2.1) Design of Primer and PCR On the basis of the base sequence of the gene of each antibody, primers for mutating the 80th amino acid residue in the variable region and the 171th amino acid residue in the constant region in the light chain to cysteine were designed. For comparison, primers for mutating the 108th amino acid residue in the variable region and the 171th amino acid residue in the constant region in the light chain of the mouse anti-insulin antibody to cysteine were designed. In view of the structure of the antibody molecule, the distance between the 108th and 171th amino acid residues in the light chain is similar to the distance between the 80th and 171th amino acid residues in the light chain where a disulfide bond can be formed. The base sequence of each primer is shown below.

[Primers of Rabbit Anti-AFP Antibody]

```
variable region
                                    (SEQ ID NO: 1)
   FOR:     5'- TGTGAAGATGCTGCCACTTATTAC -3'

(SEQ ID NO: 2)
   REV:     5'- CGTCACGCCACTGATGGTGA -3' constant region
                                    (SEQ ID NO: 3)
   FOR:     5'- TGTACCTACAGCCTGAGCAGCAC -3'

(SEQ ID NO: 4)
   REV:     5'- GTCTTCGGGGCTCTGCGGTG -3'
```

[Primer of Human Anti-HER2 Antibody]

```
variable region
                                    (SEQ ID NO: 5)
   FOR:     5'- TGTGAAGACTTCGCCACGTATTAC -3'

(SEQ ID NO: 6)
   REV:     5'- CTGCAGAGAGCTGATCGTCAGG -3' constant region
                                    (SEQ ID NO: 7)
   FOR:     5'- TGTACGTACAGCCTGAGTTCCACC -3'

(SEQ ID NO: 8)
   REV:     5'- GTCTTTTGAATCTTGTTCGGTCACGG -3'
```

[Primers of Mouse Anti-Insulin Antibody]

```
variable region (80th)
                                    (SEQ ID NO: 9)
   FOR:     5'- TGTGAAGATGCTGCCACTTATTAC -3'

(SEQ ID NO: 10)
   REV:     5'- CTCCATGCTGCTGATTGTGAG -3' variable region (108th)
                                    (SEQ ID NO: 11)
   FOR:     5'- TGTGCTGATGCTGCACCAACTGTATC -3'

(SEQ ID NO: 12)
   REV:     5'- TCTGATTTCCAGCTTGGTGCC -3' constant region
                                    (SEQ ID NO: 13)
   FOR:     5'- TGTACCTACAGCATGAGCAGCAC -3'

(SEQ ID NO: 14)
   REV:     5'- GTCTTTGCTGTCCTGATCAG -3'
```

Using a plasmid DNA containing the gene of each antibody as a template, a PCR reaction solution having the following composition was prepared.
[PCR Reaction Solution]

| | |
|---|---|
| 10x PCR buffer | 5 µL |
| 25 mM Mg$_2$SO$_4$ | 3 µL |
| 2 mM dNTP mix | 5 µL |

-continued

| | |
|---|---|
| forward primer | 1 μL |
| reverse primer | 1 μL |
| plasmid DNA (40 ng/μL) | 0.5 μL |
| KOD plus neo (1 U/μL) | 1 μL |
| purified water | 33.5 μL |
| total | 50 μL |

The prepared PCR reaction solution was subjected to a PCR reaction under the following reaction conditions.
[Reaction Conditions]
30 cycles each including 2 minutes at 98° C., 10 seconds at 98° C., 30 seconds at 54° C. and 4 minutes at 68° C., and 3 minutes at 68° C.

2 μL of DpnI (10 U/μL) was added to the obtained PCR product (50 μL) to fragment the PCR product. Using the DpnI-treated PCR product, a ligation reaction solution having the following composition was prepared. The reaction solution was incubated at 16° C. for 1 hour to carry out a ligation reaction.
[Ligation Reaction Liquid]

| | |
|---|---|
| DpnI-treated PCR product | 2 μL |
| Ligation high ver. 2 | 5 μL |
| T4 polynucleotide kinase | 1 μL |
| purified water | 7 μL |
| total | 15 μL |

(2.2) Examination of Transformation, Plasmid DNA Extraction and Sequence

A solution (3 μL) after the ligation reaction was added to DH5α (30 μL), and the same procedure as described in (1.3) above was carried out to obtain a transformant of E. coli. A plasmid DNA was extracted from the obtained E. coli using QIAprep® Spin Miniprep Kit. The base sequence of each plasmid DNA obtained was identified using a pCDNA™ 3.4 vector primer. Subsequently, these plasmid DNAs were used as plasmids for expression of ian cells.
(3) Expression in Mammalian Cells
[Reagents]
Expi 293 (trademark) Cells (Invitrogen Company)
Expi 293 (trademark) Expression Medium (Invitrogen Company)
ExpiFectamine (trademark) 293 Transfection Kit (Invitrogen Company)
(3.1) Transfection Expi 293 cells were grown by performing shaking culture (150 rpm) at 37° C. in a 5% $CO_2$ atmosphere. 30 mL of cell cultures (3.0×10⁶ cells/mL) were provided, where the number of cell cultures corresponded to the number of samples. Using a plasmid DNA encoding wild type and mutant type of each antibody, a DNA solution having the following composition was prepared, and left standing for 5 minutes.

[DNA Solution]

| | |
|---|---|
| Light chain plasmid solution | amount (μL) equivalent to 15 μg |
| Heavy chain plasmid solution | amount (μL) equivalent to 15 μg |
| Opti-MEM (trademark) | appropriate amount (mL) |
| total | 1.5 mL |

A transfection reagent having the following composition was prepared, and left standing for 5 minutes.

| | |
|---|---|
| ExpiFectamine reagent | 80 μL |
| Plasmid solution | 1420 μL |
| total | 1.5 mL |

The prepared DNA solution and transfection reagent were mixed, and the mixture was left standing for 20 minutes. The resulting mixed liquid (3 mL) was added to the cell culture (30 mL), and shaking culture (150 rpm) was performed at 37° C. in a 5% $CO_2$ atmosphere for 20 hours. After 20 hours, 150 μL and 1.5 mL of ExpiFectamine (trademark) transfection enhancers 1 and 2, respectively, were added to each culture, and shaking culture (150 rpm) was performed at 37° C. in a 5% $CO_2$ atmosphere for 6 days.
(3.2) Recovery and Purification of Antibody Each cell culture was centrifuged at 3000 rpm for 5 minutes, and the culture supernatant was recovered. The culture supernatant contains each antibody secreted from transfected Expi 293™ cells. The obtained culture supernatant was centrifuged again at 15000×G for 10 minutes, and the supernatant was recovered. The obtained supernatant was purified using a HiTrap® Protein A HP column (GE Healthcare). The resulting solution was further purified using a Superdex® 200 Increase 10/300 GL column (GE Healthcare) to obtain an antibody solution. A specific procedure for purification was carried out in accordance with the attached document of each column.
(4) Results A wild type of each of a rabbit anti-AFP antibody and a human anti-HER2 antibody, and a mutant type (cys 80-171) as a modified antibody thereof were obtained. A wild-type of a mouse anti-insulin antibody, and a mutant type (cys 80-171) and a mutant type (cys 108-171) as modified antibodies thereof were obtained. Details of the mutant type of each antibody are shown below.

Table 2 shows the amino acid sequences of the light chains (κ) of the wild type (clone A1) of the rabbit anti-AFP antibody and the mutant type thereof. In the following table, the "mutant type (cys80-171)" refers to an antibody in which the 80th amino acid residue in a variable region and the 171th amino acid residue in a constant region in the wild-type antibody are substituted with cysteine. The underlined sections each indicate a variable region, and residues surrounded by a square each indicate the 80th amino acid residue in the variable region and the 171th amino acid residue in the constant region based on the Kabat method.

TABLE 2

Light chain of wild type of rabbit anti-AFP antibody (SEQ ID NO: 15)
ELVLTQTPSSVSAAVGGTVTINCQASQSVSNLLAWYQQKPGQPPKLLIYGASNLESGVPSRFRGSGS GTQFTLTISGVT<u>A</u>EDAATYYCQSGYYSTGAITFGKGTKLEIKRDPVAPSVLLFPPSKEELTTGTATIVC

VANKFYPSDITVTWKVDGTTQQSGIENSKTPQSPEDNTYSLSSTLSLTSAQYNSHSVYTCEVVQGSA

TABLE 2-continued

SPIVQSFNRGDC

Light chain of mutant type (cys 80-171) of rabbit anti-AFP antibody (SEQ ID NO: 16)
<u>ELVLTQTPSSVSAAVGGTVTINCQASQSVSNLLAWYQQKPGQPPKLLIYGASNLESGVPSRFRGSGS</u>

<u>GTQFTLTISGVT</u>[C]EDAATYYCQSGYYSTGAITFGKGTKLEIKRDPVAPSVLLFPPSKEELTTGTATIVC

VANKFYPSDITVTWKVDGTTQQSGIENSKTPQSPED[C]TYSLSSTLSLTSAQYNSHSVYTCEVVQGSA

SPIVQSFNRGDC

---

Table 3 shows the amino acid sequences of the light chains (κ) of the wild type (trastuzumab) of the human anti-HER2 antibody and the mutant type thereof. The underlined sections each indicate a variable region, and residues surrounded by a square each indicate the 80th amino acid residue in the variable region and the 171th amino acid residue in the constant region based on the Kabat method.

filtration. The fraction containing each antibody was diluted with PBS to prepare a sample (final concentration: 5 μM). The Tm value of each antibody was measured using MicroCal PEAQ-DSC (Malvern Instruments Ltd.). Conditions for gel filtration and DSC measurement are identical to the conditions described in the reference example.

TABLE 3

Light chain of wild type of human anti-HER2 antibody (SEQ ID NO: 17)
<u>DIQMTQSPSSLSASVGDRVTITCRASQDVNTAVAWYQQKPGKAPKLLIYSASFLYSGVPSRFSGSRSG</u>

<u>TDFTLTISSLQ</u>[P]EDFATYYCQQHYTTPPTFGQGTKVEIKRTVAAPSVFIFPPSDEQLKSGTASVVCLLN

NFYPREAKVQWKVDNALQSGNSQESVTEQDSKD[S]TYSLSSTLTLSKADYEKHKVYACEVTHQGLSLP

VTKSFNRGEC

Light chain of mutant type (cys 80-171) of human anti-HER2 antibody (SEQ ID NO: 18)
<u>DIQMTQSPSSLSASVGDRVTITCRASQDVNTAVAWYQQKPGKAPKLLIYSASFLYSGVPSRFSGSRSG</u>

<u>TDFTLTISSLQ</u>[C]EDFATYYCQQHYTTPPTFGQGTKVEIKRTVAAPSVFIFPPSDEQLKSGTASVVCLLN

NFYPREAKVQWKVDNALQSGNSQESVTEQDSKD[C]TYSLSSTLTLSKADYEKHKVYACEVTHQGLSLP

VTKSFNRGEC

---

The mutant type (cys80-171) of the mouse anti-insulin antibody is an antibody in which the 80th alanine residue in the variable region and the 171th serine residue in the constant region in the light chain (κ) of the wild-type antibody are substituted with cysteine. The mutant type (cys108-171) of the mouse anti-insulin antibody is an antibody in which the 108th alanine residue in the variable region and the 171th serine residue in the constant region in the light chain (κ) of the wild-type antibody are substituted with cysteine.

Example 2: Thermal Stability of Modified Antibody

The thermal stability of the wild type of each antibody prepared in Example 1, and the mutant type thereof was examined.
(1) Measurement of Thermal Stability
The solvent of a solution containing each antibody obtained in Example 1 was replaced by PBS (pH 7.4) by gel (2) Results
The Tm values of the antibodies, which were obtained by DSC measurement, are shown in Tables 4 to 7. The analytical peaks of the antibodies are shown in FIGS. 1, 2, and 3A to 3C.

TABLE 4

| Rabbit anti-AFP antibody (IgG) | Tm (° C.) |
|---|---|
| Wild type | 76.6 |
| Mutant type (cys80-171) | 80.0 |

TABLE 5

| Human anti-HER2 antibody (Fab) | Tm (° C.) |
|---|---|
| Wild type | 80.9 |
| Mutant type (cys80-171) | 84.4 |

TABLE 6

| Mouse anti-insulin antibody (IgG) | Tm (° C.) |
|---|---|
| Wild type | 76.4 |
| Mutant type (cys80-171) | 80.1 |

TABLE 7

| Mouse anti-insulin antibody (Fab) | Tm (° C.) |
|---|---|
| Wild type | 77.3 |
| Mutant type (cys80-171) | 80.6 |
| Mutant type (cys108 -171) | 75.2 |

As shown in Tables 4 to 7, the Tm value of the mutant type (cys80-171) of each of the rabbit antibody, the human antibody and the mouse antibody was higher than that of the wild type of each of the antibodies by 3° C. or more. Thus, it has been shown that when in an antibody in which the 80th amino acid residue in the variable region and the 171th amino acid residue in the constant region based on the Kabat method is not cysteine, these amino acid residues are substituted with cysteine, the thermal stability of the antibody can be improved. Arai H. et al., Crystal structure of a conformation-dependent rabbit IgG Fab specific for amyloid prefibrillar oligomers, Biochim Biophys Acta. Vol. 1820, p. 1908-1914, 2012 suggests that in a rabbit antibody, a disulfide bond is formed between the 80th and 171th cysteic acid residues cysteic acid residues in the light chain, and thus a disulfide bond is likely formed in the mutant type (cys80-171) of each antibody as well. Therefore, improvement of thermal stability by introduction of a cysteine residue ascribable to formation of a disulfide bond specific to a rabbit antibody of seven-SS type.

On the other hand, the Tm value of the mutant type (cys108-171) of the mouse antibody was lower than that of the wild type of the mouse antibody by 2° C. or more. As described above, the 108th and 171th amino acid residues in the light chain are situated at positions close to the 80th and 171th amino acid residues in the light chain in view of the structure of the antibody molecule. However, it was shown that when the 108th and 171th amino acid residues in the light chain were substituted with cysteine, thermal stability was deteriorated rather than being improved.

Example 3: Affinity of Modified Antibody for Antigen

Figure 4:
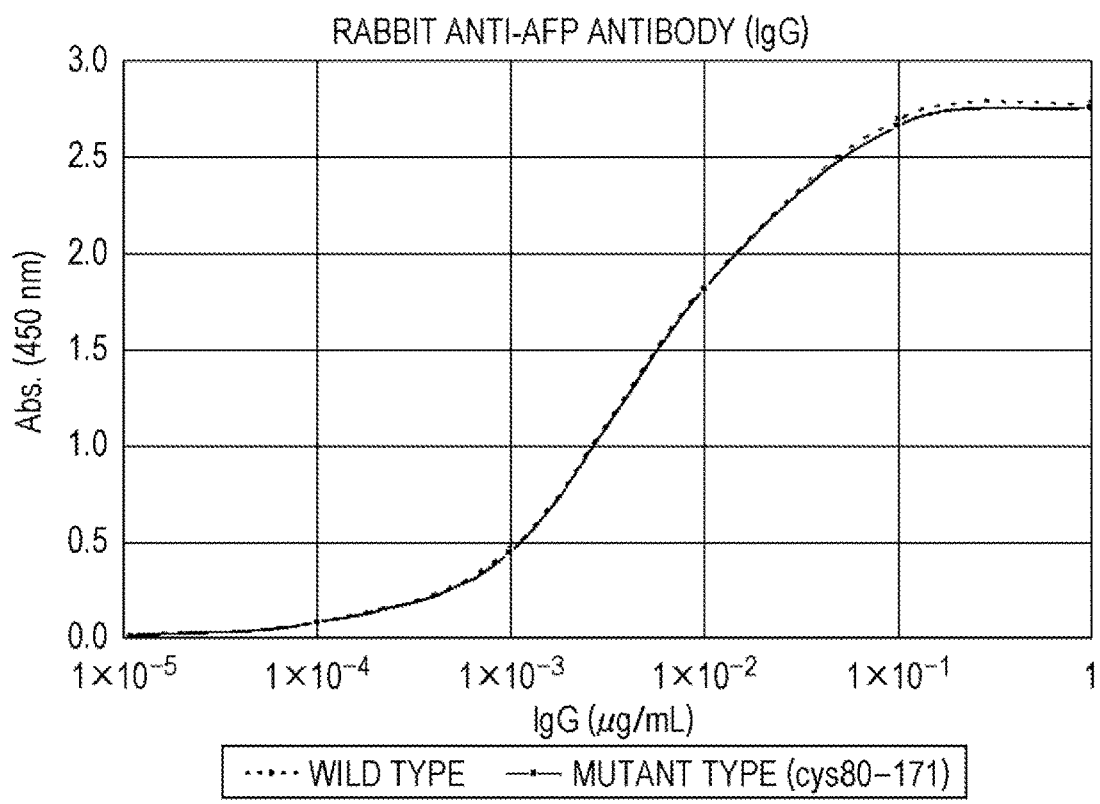
FIG. 4 is a graph showing the results of analyzing affinity of a rabbit anti-AFP antibody for wild-type and mutant-type (cys 80-171) antigens by the ELISA method.
Figure 5:
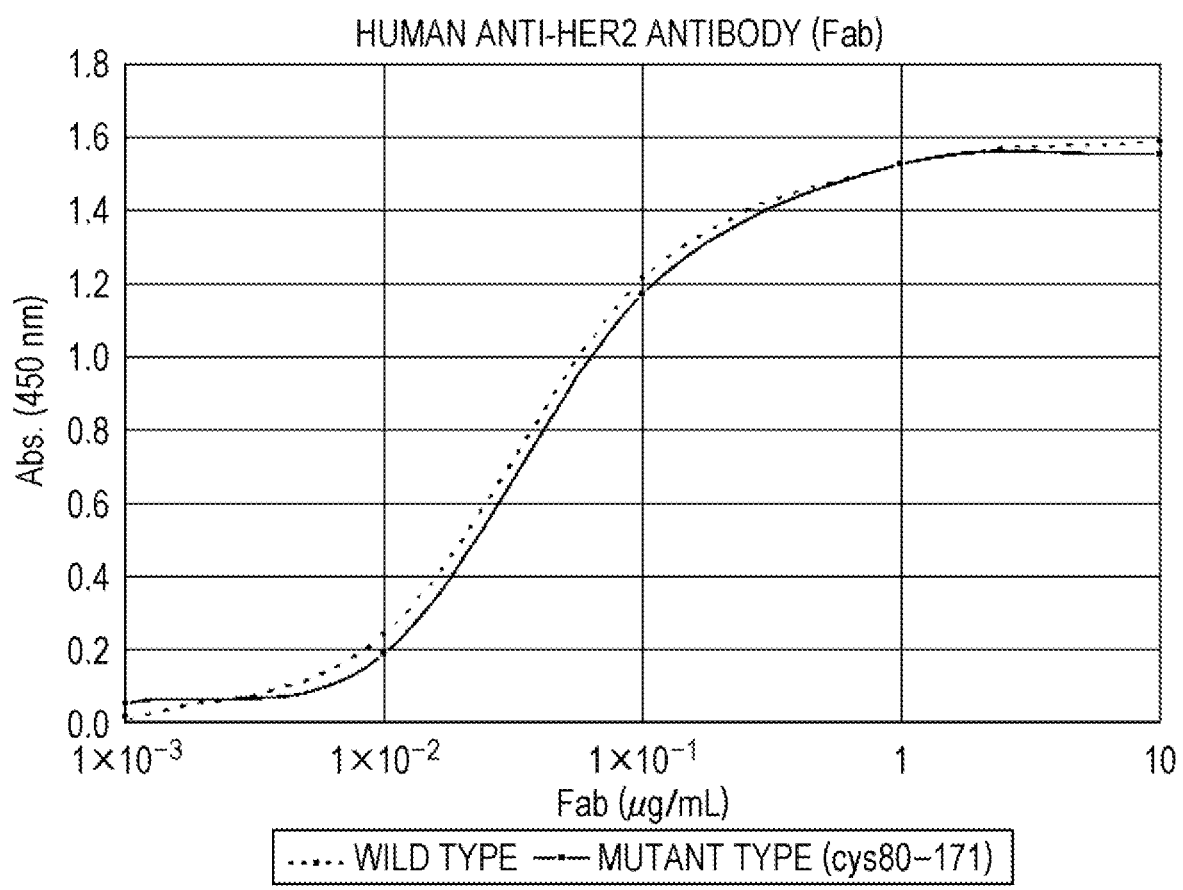
FIG. 5 is a graph showing the results of analyzing affinity of a human anti-HER2 antibody (Fab) for wild-type and mutant-type (cys 80-171) antigens by the ELISA method.
Figure 6:
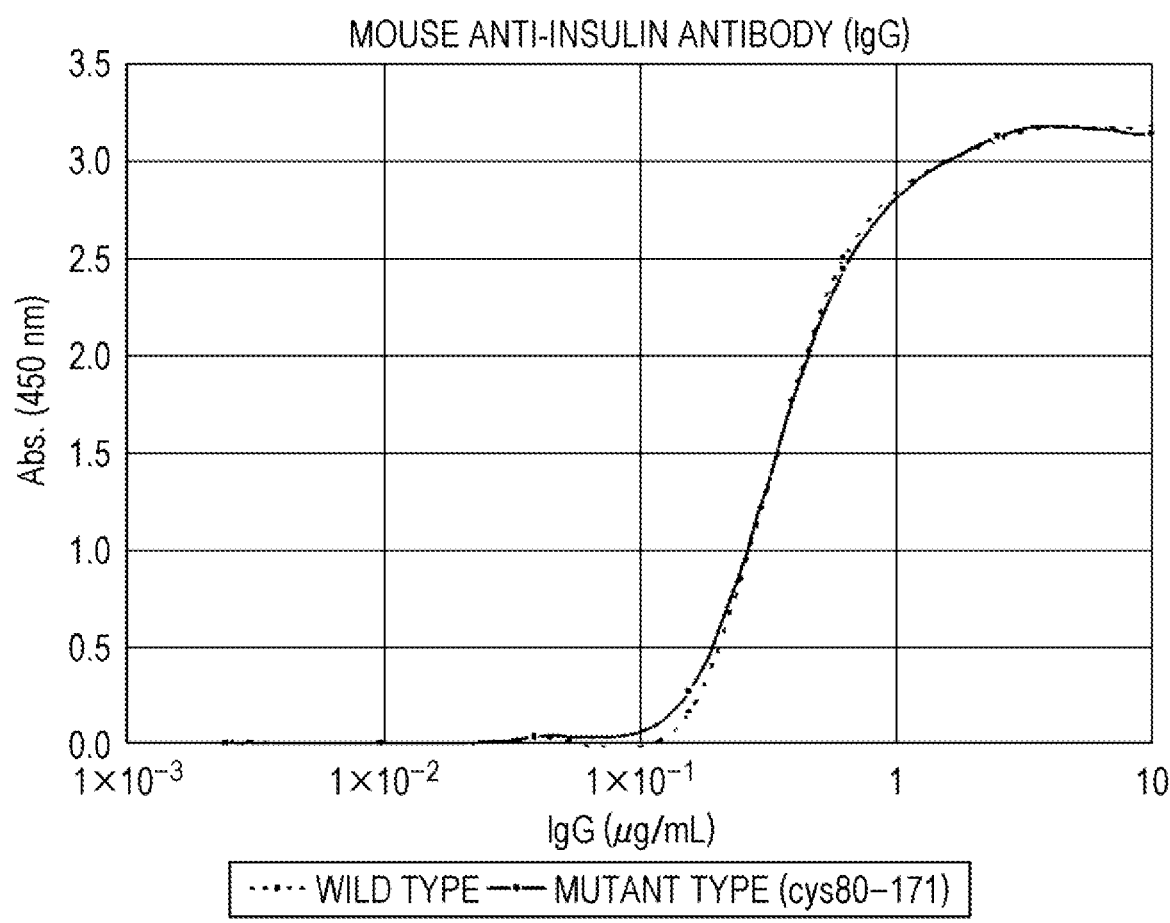
FIG. 6 is a graph showing the results of analyzing affinity of a mouse anti-insulin antibody for wild-type and mutant-type (cys 80-171) antigens by the ELISA method.

The affinity of each antibody prepared in Example 1 for the wild type of each antibody and the mutant type thereof for an antigen was examined by the ELISA method.
(1) Measurement by ELISA Method
(1.1) Antigen and Antibody for Detection As an antigen for a rabbit anti-AFP antibody, an AFP protein (Lee biosolutions, Inc., catalog number: 105-11) was used. As an antigen for a human anti-HER2 antibody, HER2 protein (R&D Systems, catalog number: 1129-ER) was used. As an antigen for a mouse anti-insulin antibody, Humulin R Injection (100 units) (Eli Lilly Company) was used. Each antibody prepared in Example 1 was stepwise diluted with 1% BSA-containing PBS to obtain a plurality of antibody solutions having different concentrations.
(1.2) Measurement Each antigen was diluted with PBS (pH: 7.4) to prepare a solution of each antigen. The solution of each antigen was added to wells of a MaxiSorp (trademark) flat bottom plate (Thermo Fisher Scientific Inc.), and left standing overnight at 4° C. The antigen solution was removed, and a blocking solution (1% BSA-containing PBS) was added to each well to perform blocking. The blocking solution was removed, and 100 µL of each antibody solution was added to each well, and an antigen-antibody reaction was carried out at room temperature for 1 hour. The antibody solution was removed, and a washing liquid (1% BSA-containing PBS) was added to each well to wash the well. After the washing, a solution of a HRP-labeled anti-rabbit Fc antibody, a HRP-labeled anti-human Fc antibody or a HRP-labeled anti-mouse Fc antibody was added according to the type of antibody for detection, and an antigen-antibody reaction was carried out at room temperature. The antibody solution was removed, and a washing liquid (1% BSA-containing PBS) was added to each well to wash the well. After the washing, a solution of an ABST substrate (Thermo Fisher Scientific Inc.) was added to each well, and the absorbance at 450 nm was measured.
(2) Results As shown in FIGS. 4 to 6, affinity for an antigen in the mutant of each of the rabbit antibody, the human antibody and the mouse antibody was almost the same as in the wild type of each of the antibodies. Therefore, substitution of the 80th amino acid residue in the variable region and the 171th amino acid residue in the constant region based on the Kabat method with cysteine has been shown to have little influence on affinity for an antigen. Thus, it has been indicated that by substituting the 80th amino acid residue in the variable region and the 171th amino acid residue in the constant region based on the Kabat method with cysteine, the thermal stability of the antibody can be improved without having no influence on affinity for an antigen.

Comparative Example: Thermal Stability of Antibody Modified at Other Sites

Studies were conducted on whether the thermal stability of the antibody was improved when amino acid residues in the vicinity of the 80th amino acid residue in the variable region and the 171th amino acid residue in the constant region based on the Kabat method in a wild-type antibody were substituted with cysteine.
(1) Production of Antibody Modified at Other Sites In the same manner as in Example 1, one selected from the 79th to 81th amino acid residues in the variable region based on the Kabat method and one selected from the 169th to 171th amino acid residues in the constant region based on the Kabat method in the wild type of a mouse anti-insulin antibody were substituted with cysteine to prepare a mutant type of the mouse anti-insulin antibody. The 80th amino acid residue in the variable region based on the Kabat method and the 170th or 171th amino acid residue in the constant region based on the Kabat method in the wild type of a human HER2 antibody were substituted with cysteine to prepare a mutant type of the human HER2 antibody.
(2) Measurement of Thermal Stability In the same manner as in Example 2, the thermal stability of the wild type of each antibody and the mutant type thereof was measured. The results are shown in Tables 8 and 9.

TABLE 8

| Mouse anti-insulin antibody (Fab) | Tm (° C.) |
|---|---|
| Wild type | 77.3 |
| Mutant type (cys80-171) | 80.6 |

TABLE 8-continued

| Mouse anti-insulin antibody (Fab) | Tm (° C.) |
|---|---|
| Mutant type (cys79-169) | 77.2 |
| Mutant type (cys79-170) | 76.6 |
| Mutant type (cys79-171) | 76.5 |
| Mutant type (cys80-169) | 76.1 |
| Mutant type (cys80-170) | 75.1 |
| Mutant type (cys81-169) | 74.9 |
| Mutant type (cys81-170) | 76.1 |
| Mutant type (cys81-171) | 74.4 |

TABLE 9

| Human anti-HER2 antibody (Fab) | Tm (° C.) |
|---|---|
| Wild type | 80.9 |
| Mutant type (cys80-171) | 84.4 |
| Mutant type (cys80-170) | 78.7 |

As shown in Tables 8 and 9, the mutant type (cys80-171) was superior in thermal stability to the wild type, but other mutant types were inferior in thermal stability to the wild type. These results show that even when amino acid residues in the vicinity of the 80th amino acid residue in the variable region and the 171th amino acid residue in the constant region based on the Kabat method in a wild-type antibody, the thermal stability of the antibody is not improved.

---

What is claimed is:

1. A method for improving thermal stability of an antibody, comprising:
   substituting the 80th amino acid residue in a light chain variable region based on the Kabat method with a cysteine residue, and substituting the 171st amino acid residue in a light chain constant region based on the Kabat method with a cysteine residue, in an original antibody in which the 80th amino acid residue in the light chain variable region and the 171st amino acid residue in the light chain constant region are not cysteine residues,
   wherein said substituting comprises providing a polynucleotide encoding an amino acid sequence of the modified antibody in which the 80th amino acid residue in the light chain variable region based on the Kabat method is a cysteine residue and the 171st amino acid residue in the light chain constant region based on the Kabat method is a cysteine residue; and producing the modified antibody,
   herein in said modified antibody, the cysteine residue introduced at said 80th amino acid residue in the light chain variable region forms an intra-chain disulfide bond with the cysteine residue introduced at said 171st amino acid residue in the light chain constant region,
   and wherein said modified antibody has improved thermal stability as compared to said original antibody.

2. The method according to claim 1, wherein said producing of said modified antibody comprises introducing the polynucleotide into a host cell; and expressing the modified antibody in the host cell.

3. The method according to claim 2, wherein said method further comprises recovering the expressed modified antibody, said recovering comprising dissolving the host cell which expresses the modified antibody and recovering the modified antibody; or recovering a culture supernatant comprising the modified antibody secreted from the host cell.

4. The method according to claim 1, wherein the original antibody is a human antibody, a mouse antibody, a rabbit antibody, a rat antibody, a pig antibody, a sheep antibody, a goat antibody, a camel antibody, a bovine antibody or a horse antibody.

5. The method according to claim 1, wherein the antibody is IgG or Fab.

6. The method according to claim 1, wherein the light chain of the antibody is a kappa chain.

7. A method for increasing Tm value and/or Tonset value of an antibody, comprising:
   substituting the 80th amino acid residue in a light chain variable region based on the Kabat method with a cysteine residue, and substituting the 171st amino acid residue in a light chain constant region based on the Kabat method with a cysteine residue, in an original antibody in which the 80th amino acid residue in the light chain variable region and the 171st amino acid residue in the light chain constant region are not cysteine residues,
   wherein said substituting comprises providing a polynucleotide encoding an amino acid sequence of the modified antibody in which the 80th amino acid residue in the light chain variable region based on the Kabat method is a cysteine residue and the 171st amino acid residue in the light chain constant region based on the Kabat method is a cysteine residue; and producing the modified antibody,
   wherein in said modified antibody, the cysteine residue introduced at said 80th amino acid residue in the light chain variable region forms an intra-chain disulfide bond with the cysteine residue introduced at said 171st amino acid residue in the light chain constant region,
   and wherein said modified antibody has increased Tm value and/or Tonset value as compared to said original antibody.

8. The method according to claim 7, wherein said producing of said modified antibody comprises introducing the polynucleotide into a host cell; and expressing the modified antibody in the host cell.

9. The method according to claim 8, wherein said method further comprises recovering the expressed modified antibody, said recovering comprising dissolving the host cell which expresses the modified antibody and recovering the modified antibody; or recovering a culture supernatant comprising the modified antibody secreted from the host cell.

10. The method according to claim 7, wherein the original antibody is a human antibody, a mouse antibody, a rabbit antibody, a rat antibody, a pig antibody, a sheep antibody, a goat antibody, a camel antibody, a bovine antibody or a horse antibody.

11. The method according to claim 7, wherein the antibody is IgG or Fab.

12. The method according to claim 7, wherein the light chain of the antibody is a kappa chain.

* * * * *